(12) United States Patent
Shi et al.

(10) Patent No.: US 10,232,080 B2
(45) Date of Patent: Mar. 19, 2019

(54) MESENCHYMAL STEM CELL-MEDIATED FUNCTION TOOTH REGENERATION

(75) Inventors: Songtao Shi, Los Angeles, CA (US); Wataru Sonoyama, Los Angeles, CA (US); Takayoshi Yamaza, Los Angeles, CA (US); Songlin Wang, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 837 days.

(21) Appl. No.: 12/514,051

(22) PCT Filed: Nov. 29, 2007

(86) PCT No.: PCT/US2007/085971
§ 371 (c)(1),
(2), (4) Date: Apr. 21, 2010

(87) PCT Pub. No.: WO2008/067488
PCT Pub. Date: Jun. 5, 2008

(65) Prior Publication Data
US 2010/0196854 A1    Aug. 5, 2010

Related U.S. Application Data

(60) Provisional application No. 60/867,751, filed on Nov. 29, 2006.

(51) Int. Cl.
*A61L 27/34* (2006.01)
*A61L 27/12* (2006.01)
*A61C 8/02* (2006.01)
*A61L 27/38* (2006.01)
*A61C 8/00* (2006.01)

(52) U.S. Cl.
CPC .............. *A61L 27/34* (2013.01); *A61L 27/12* (2013.01); *A61L 27/3834* (2013.01); *A61L 27/3865* (2013.01); *A61L 27/3891* (2013.01); *A61C 8/0006* (2013.01); *A61C 8/0043* (2013.01)

(58) Field of Classification Search
CPC .. A61L 27/34; A61L 27/3865; A61L 27/3891; A61L 27/3834
See application file for complete search history.

(56) References Cited

U.S. PATENT DOCUMENTS

| 4,671,770 A * | 6/1987 | Bell et al. ..................... 433/223 |
| 6,589,525 B2 * | 7/2003 | Gault ............................ 424/93.7 |
| 7,052,907 B2 | 5/2006 | Shi et al. ....................... 435/325 |
| 2003/0175656 A1 * | 9/2003 | Livne et al. ............... 433/201.1 |
| 2009/0162326 A1 * | 6/2009 | Siemonsmeier et al. .... 424/93.7 |

FOREIGN PATENT DOCUMENTS

WO       WO02/07679    * 1/2001

OTHER PUBLICATIONS

Shi et al J Bone Miner Res 2003, 18: 696-704).*
Young et al Tissue Engg 2005, 11( 9/10), 2005, 1599-1610.*
Seo et al Lancet. Jul. 10-16, 2004; 364(9429):149-55.*
Harada et al Journal of Cell Biology, 147(1), 105-120, 2004.*
Magnaldo et al Journal of Cell Science, 1996, 19, 3035-3045.*
Samstein et al Journal of American Society of Nephrology 12: 182-193, 2001.*
Spangers Kidney International (2008) 74, 14-21.*
Fred Gage Nature 392: 18-24, 1998.*
Sonoyams et al PLoS ONE, 2006, E79, 1-8.*
Ruparel et al (J Endod. 2013, 39(3):357-63, abstract only.*
Nakao et al (BBRC, vol. 325, No. 3, 2004, pp. 1052-1059.*
Gomez Flores et al, (Journal of Periodontal Research, vol. 43, No. 3, 2008, pp. 364-371, abstract only, p. 1-2.*
Shirsawa et al Developmental Dynamics, 1993, 188, 1-13).*
Sonoyama et al PLoS One, 2006, e79, 1-8.*
Huang et al (Stem cells and dental tissue reconstruction and Craniofacial Reconstruction, Ed.Spencer and Misra, p. 325-352 Year: 2016).*
Abe et al Oral Science International, 45-58 (Year: 2007).*
Zhang et al, "Proliferation and odontogenic differentiation of BMP2 gene-transfected stem cells from human tooth apical papilla . . . ", International Journal of Molecular Medicine, No. 34, pp. 1004-1012, 2014.
Pettinger et al, "Multilineage Potential of Adult Human Mesenchymal Stem Cells," www.sciencemag.org, Science, vol. 284, Apr. 2, 1999.
Young et al., "Adult Stem Cells," The Anatomical Record Part A 276A, pp. 75-102, 2004.
Le Blanc et al., "A Comparison of Nonmyeloablative and Reduced-Intensity Conditioning for Allogenic Stem-Cell Transplantation," Clinical Transplantation, vol. 78, No. 7, Oct. 15, 2004.
Le Blanc et al., "Treatment of severe acute graft-versus-host disease with third party haploidentical . . . ", Research Letters, The Lancet, vol. 363, May 1, 2004.
Trubiani et al., "Morphological and cytofluorimetric analysis of adult mesenchymal stem cells expanded . . . ," International Journal of Immunopathology and Pharmacology, vol. 18, Issue 2, pp. 213-221, Apr.-Jun. 2005.
D'Aquino et al., "Human postnatal dental pulp cells co-differentiate into osteoblasts and endotheliocytes . . . ," Cell Death and Differentiation (2007) 14, Nature Publishing Group, pp. 1162-117, All rights reserved 1350-9047/07.

(Continued)

*Primary Examiner* — Anoop K Singh
(74) *Attorney, Agent, or Firm* — McDermott Will & Emery LLP (57) ABSTRACT

A method for reconstructing a functional tooth by using a carrier loaded with a plurality of mesenchymal stem cells including at least one of a stem cell derived from Apical Papilla (SCAP), Periodontal Ligament Stem Cells (PDLSC), and Dental Pulp Stem Cells (DPSC). The mesenchymal stem cell loaded carrier is planted into a site within a subject's oral cavity to form a bio-root upon which a crown may be affixed, The mesenchymal stem cells will develop new periodontal tissues to stabilize the bio-root. Methods disclosed herein are particularly beneficial for subjects lacking good bone structures for conventional crown treatments.

8 Claims, 5 Drawing Sheets

(56) References Cited

OTHER PUBLICATIONS

Lindroos et al., Characterisation of human dental stem cells and buccal mucosa fibroblasts, ScienceDirect, Elsevier Inc., Biochemical and Biophysical Research Communications, 368 (2008) 329-335.

Wei, et al., "Functional Tooth Restoration by Allogeneic Mesenchymal Stem Cell-Based Bio-Root Regeneration in Swine," Stem Cells and Development, vol. 22, No. 12, 2013.

Sun et al., "Mesenchymal Stem Cell Transplantation Reverses Multiorgan Dysfunction in Systemic Lupus Erythematosus . . . ," Stem Cells, 2009; 27,1421-1432.

Bakopoulou et al., "Comparative analysis of in vitro osteo/odontogenic differentiation potential of human dental pulp stem cells . . . ," Archives of Oral Biology, 56 (2011) 709-721.

Wu et al., "Basic Fibroblast Growth Factor Enhances Stemness of Human Stem Cells from the Apical Pipilla," NIH Public Access, J Endod. May 2012 ; 38(5): 614-622. doi:10.1016/j.joen.2012.01.014.

Bakopoulou et al., "Comparative characterization of STRO-1neg/CD146pos and . . . ," SciVerse ScienceDirect, Archives of Oral Biology 58 (2013) 1556-1568.

Ruparel et al., "Characterization of a Stem Cell of Apical Papilla Cell Line: Effect of Passage on Cellular Phenotype," Basic Research—Biology, JOE—vol. 39, No. 3, Mar. 2013.

\* cited by examiner

MESENCHYMAL STEM CELL-MEDIATED FUNCTION TOOTH REGENERATION

CROSS-REFERENCE TO RELATED APPLICATIONS

This application claims an invention which was disclosed in U.S. Provisional Application No. 60/867,751 filed Nov. 29, 2006, entitled "MESENCHYMAL STEM CELL-MEDIATED FUNCTIONAL TOOTH REGENERATION". The benefit under 35 USC § 119(e) of the United States provisional application is hereby claimed. The above priority application is hereby incorporated herein by reference.

STATEMENT OF FEDERALLY SPONSORED RESEARCH AND DEVELOPMENT

This invention was made, at least in part, with grants awarded by NIDCR/NIH, and in part by National Natural Science Foundation of China (Grant No. 30428009) and Beijing Major Scientific Program grant (Grant No. D0906007000091). The Government and funding agencies have certain rights in the invention.

FIELD OF THE INVENTION

The present invention, in general, relates to tissue regeneration. In particular, the present invention relates to a new population of mesenchymal stem cells isolated from the root apical papilla of human teeth and methods for utilizing the stem cells in the regeneration of tooth.

BACKGROUND OF THE INVENTION

Regeneration of a functional and living tooth is a highly desirable approach for the replacement of a diseased or damaged tooth (1-3). Recent advances in dental stem cell biotechnology and cell-mediated murine tooth regeneration have encouraged researchers to explore the potential for regenerating living teeth with appropriate functional properties (4-6). It has been shown that murine teeth can be regenerated using many different stem cells to collaboratively form dental structures in vivo (4, 5, 7). In addition, dentin/pulp tissue and cementum/periodontal complex have been regenerated from human dental pulp stem cells (DPSCs) and periodontal ligament stem cells (PDLSCs), respectively, when transplanted into immunocompromised mice (8, 9). However, owing to the complexity of human tooth growth and development, the regeneration of a whole tooth structure, including enamel, dentin/pulp complex, and periodontal tissues, has not been possible by using currently available regenerative biotechnologies.

From a clinical perspective, the most important part of the tooth is the root which is required to support a (natural or artificial) crown; the crown alone cannot fulfill normal tooth function without a viable root. The spatially and temporally organized microenvironment of the tooth bud and its surrounding tissues permits growth and development of the crown and roots, resulting in formation and eruption of the tooth (10). Root development involves dentin formation, cementum generation, instruction of epithelium, and tooth eruption. Thus, the re-generation of a whole tooth is highly complicated and technically challenging. In contrast, the lesser challenging goal of replacing a damaged crown with a synthetic crown has been widely applied in dental clinics with excellent therapeutic outcomes (11).

However, despite the fact that dental implant therapies have achieved long-term success in the clinic for recovering tooth function, successful implantations require preexisting high-quality bone structures for supporting the implants (12, 13). Subjects who lack good bone structures are currently unable to benefit from such therapies. Hence, reconstruction of teeth in patients without adequate bone support would be a major advance.

Accordingly, there exits a need for improved therapeutic methods that can repair or replace damaged tooth in subjects who lack adequate bone support structures for tooth implants.

SUMMARY OF THE INVENTION

In view of the foregoing, it is an objective of the present invention to provide a method for reconstructing a functional tooth in subjects suffering from dental diseases. To this end, stem cell-mediated root regeneration offers opportunities to regenerate a bio-root and its associated periodontal tissues, which are necessary for maintaining the physiological function of teeth.

The inventors of the present invention have unexpectedly discovered and successfully isolated a novel population of mesenchymal stem cells from apical papilla (SCAP) that is capable of differentiating into odontoblastic/osteoblastic cells. Based on this discovery the inventors have developed tooth repair methods of the present invention.

Specifically, in one aspect, the present invention provides a novel population of mesenchymal stem cells isolated from human root apical papilla tissue, wherein the stem cells are capable of differentiating into odontoblastic/osteoblastic cells.

In another aspect, the present invention provides a method for reconstructing a functional tooth in a subject, in which a bio-root periodontal complex is built up by postnatal stem cells including SCAP and periodontal ligament stem cells (PDLSCs), to which an artificial porcelain crown can then be affixed.

The hybrid strategy of this aspect of the present invention has at least the following advantages. By leveraging existing dental repair technology such as artificial crowns, the present invention side-steps the challenging task of regenerating a whole tooth structure, and effectively enables recovery of tooth strength, function, and appearance in subjects who lack adequate bone structures.

Autologous dental stem cell engineering may also be applied to tooth regeneration in species having closely related dental tissues such as human, murine, swine, and simian.

Furthermore, functional tooth restoration in non-human species, such as swine, may also provide a research tool in the form of animal models (14, 15).

Other aspects and advantages of the invention will be apparent from the following description and the appended claims.

BRIEF DESCRIPTION OF THE DRAWINGS

FIG. 1 shows the isolation of Stem Cells from Root Apical Papilla. (A) Human apical papilla tissue was positive for STRO-I, an early mesenchymal progenitor marker, staining by immunofluorescence (arrows). (B) Single colonies were formed after human SOAP were plated at a low density ($5 \times 10^3$/T25 flask) and cultured for 10 days. (C) When human SOAP were cultured in odontogenic/osteogenic inductive conditions containing L-ascorbate-2-phosphate, dexamethasone, and inorganic phosphate for 4 weeks, mineralized nodules were found by Alizarin red S staining. (D) Cultured human SCAP formed Oil red O positive lipid clusters following 5 weeks of adipogenic induction in the presence of 0.5 mM isobutylmethylxanthine, 0.5 µM hydrocortisone, 60 [mu]M indomethacin, and 10 µg/ml insulin. (E) Eight weeks after transplantation in immunocompromised mice, human SCAP differentiated into odontoblasts (arrows) that formed dentin (D) on the surfaces of a hydroxyapatite tricalcium (HA) carrier. (F) Immunohistochemical staining showed that human SOAP differentiated into odontoblasts (arrows) that were positive for anti-human specific mitochondria antibody staining. (G) Immunohistochemical staining showed that human SOAP-generated dentin (D) was positive for anti-DSP antibody staining (arrows). (H) Pre-immunoserum negative control of human SOAP transplant. (I) SOAP isolated from swine were capable of forming a single colony cluster when plated at a low cell density. (J) When transplanted into immunocompromised mice for 8 weeks, swine SOAP differentiate into odontoblasts (arrows) to regenerate dentin (D) on the surface of the hydroxyapatite carrier (HA). (K) Swine PDLSCs were capable of forming a single colony cluster. (L) After transplantation into immunocompromised mice, swine PDLSCs formed cementum (C) on the surface of hydroxyapatite carrier (HA). Collagen fibers were found to connect to newly formed cementum.

FIG. 2 shows the characterization of human SCAP in comparison with DPSCs. (A) Western blot analysis to confirm protein expression of genes identified in microarray studies showed greater abundance of survivin in SOAP than in DPSCs, with similar levels of DSP and Cbfal/Runx2. (B) Flow cytometric analysis showed that ex vivo expanded SOAP contained approximately 7.5% CD24-positive cells, but DPSCs exhibited 0.5% positive staining for CD 24. (C) The proliferation rates of SOAP and DPSCs, derived from the same tooth, were assessed by co-culture with BrdU for 6 hours. The number of BrdU positive cells was presented as a percentage of the total number of cells counted from five replicate cultures. SOAP showed a significantly higher proliferation rate in comparison with DPSCs (*P=0.0042). (D) Single colony-derived SOAP were able to proliferate to over 70 population doublings, which was significantly higher than DPSCs (*P=0.0192). (E) Dentin regeneration capacity of SOAP was significantly higher than that of DPSCs when transplanted into the same immunocompromised mice (*P=0.0489) using Scion Image analysis system (Scion Image, Rockville, Md.). (F) SOAP showed a significant higher telomerase activity than DPSCs at passage 1 (*P=0.015). Cultured BMMSCs at passage 1 were used as a negative control to show an absence of telomerase activity. The telomerase activity was assessed by real time PCR based quantitative telomerase detection kit as described in Materials and Methods. (G) Cell motility assessed by a scratch assay. A representative area of SOAP and DPSCs at 72 hours after scratch was presented. Red arrows indicate the ranges of cell migration during 72 hours (*P=0.0033).

FIG. 3 shows data that characterize the surface molecules of human SOAP, (A) Flow cytometric analysis of cultured SCAP at passage 1 revealed expression of STRO-I (18.12%), CD146 (72.3%), CD24 (7.56%), CD166 (93.74%), CD73 (94.14%), CD90 (95.54%), CD105 (9.23%), CD106 (32.7%), CD29 (88.1%) and ALP (11.43%), but was negative for surface molecules CD18, CD14, CD34, CD45, and CD 150. (B) After 2 weeks osteoinduction in vitro with L-ascorbate-2-phosphate, dexamethasone, and inorganic phosphate, SOAP differentiated into odontoblasts with a decrease in CD24 expression from 7.56% to 0.22%. In contrast, ALP expression increased significantly from 11.43% to 86.59%.

FIG. 5 shows swine SCAP/PDLSC-mediated root/periodontal structure as an artificial crown support for the restoration of tooth function in swine. (A) Extracted minipig lower incisor and root-shaped HA/TCP carrier loaded with SCAP. (B) Gelfoam containing 10×106 PDLSCs (open arrow) was used to cover the HAISCAP (black arrow) and implanted into the lower incisor socket (open triangle). (C) HA/SCAP-Gelfoam/PDLSCs were implanted into a newly extracted incisor socket. A post channel was pre-created inside the root shape HA carrier (arrow). (D) The post channel was sealed with a temporary filling for affixing a porcelain crown in the next step. (E) The HAISCAP-Gelfoam/PDLSC implant was sutured for 3 months. (F) The HA/SCAP-Gelfoam/PDLSC implant (arrow) was re-exposed and the temporary filling was removed to expose the post channel. (G) A pre-made porcelain crown was cemented to the HA/SCAP-Gelfoam/PDLSC structure. (H) The exposed section was sutured. (I and J) Four weeks after fixation, the porcelain crown was retained in the swine after normal tooth use as shown by open arrows. (K) After 3 months implantation, the HA/SCAP-Gelfoam/PDLSC implant had formed a hard root structure (open arrows) in the mandibular incisor area as shown by CT scan image. A clear PDL space was found between the implant and surrounding bony tissue (triangle arrows). (L and M) H&E staining showed that implanted HA/SCAP-Gelfoam/PDLSC contains newly regenerated dentin (D) inside the implant (L) and PDL tissue (PDL) on the outside of the implant (M). (N) Compressive strength measurement showed that newly formed bio-roots have much higher compressive strength than original HA/TCP carrier (*P=0.0002), but lower than that in natural swine root dentin (*P~0.003) (NR: natural minipig root, BR; newly formed bio-root, HA: original HA carrier).

DETAILED DESCRIPTION

As noted above, the present invention is based on the unexpected discovery of a novel population of mesenchymal stem cell isolated from the root apical papilla of human teeth. The inventors of the present invention have successfully isolated and cultured this novel mesenchymal stem cell and developed methods for repairing damaged tooth by utilizing the mesenchymal stem cells of the present invention.

In general, methods of the present invention utilizes the unique properties of mesenchymal stem cells in such a way that a bio-root may be grown into the subject's oral skeletal-muscular structure, which will then provide an anchoring point to affix conventional crowns. Accordingly, in one aspect, the present invention provides a method for repairing a damaged tooth in a subject, having the general steps of: (1) providing a root-shaped biocompatible carrier formed in a shape resembling a root of the damaged tooth, loaded with SOAP, and coated with PDLSC, and wherein the carrier has an inner post channel space; (2) extracting the damaged tooth from the subject's oral cavity, wherein upon extraction of the damaged tooth, an extraction socket is formed in its place; (3) cleaning the extraction socket and implanting the root-shaped biocompatible carrier into the socket; (4) allowing sufficient time for the SOAP and PDLSC to form a bio-root incorporating the carrier; and (5) surgically exposing the biocompatible carrier and affixing a pre-fabricated crown resembling the damaged tooth onto the bio-root.

For the purpose of the present invention, suitable biocompatible carrier may be made of any biocompatible material having physical properties such as strength, hardness, etc. that are suitable for use as a dental root. Exemplary biocompatible materials may include hydroxyapatite, tricalcium phosphate, or any other suitable biocompatible material commonly known in the art.

Once the bio-root is formed and become strong, it may be treated as a natural root. Conventional dental treatments such as crowning may then be used. Suitable crowns may be porcelain crowns, metal crowns, or any other types of crowns commonly known in the art.

Having generally described the present invention, reference is now made to the following specific examples along with the accompanying figures to facilitate a full understanding of the present invention.

It should be noted that although the present invention will be described in terms of specific exemplary embodiments and examples below, a person skilled in the relevant art will appreciate that the embodiments disclosed herein are for illustrative purposes only and various modifications and alterations might be made by those skilled in the art without departing from the spirit and scope of the invention as set forth in the following claims.

EXAMPLES

Materials and Methods
Subjects and Cell Culture

Normal human impacted third molars (n=18) were collected from sixteen adults (18-20 yr of age) at the Dental Clinic of the National Institute of Dental & Craniofacial Research (NIDCR) under approved guidelines set by NIH Office of Human Subjects Research and University of Southern California IRB. Root apical papilla was gently separated from the surface of the root, minced and digested in a solution of 3 mg/ml collagenase type I (Worthington Biochemicals Corp., Freehold, N.J.) and 4 mg/ml dispase (Roche Diagnostic/Boehringer Mannheim Corp., Indianapolis, Ind.) for 30 minutes at 37° C. Single cell suspensions of SCAP were obtained by passing through a 70 µm strainer (Falcon, BD Labware, Franklin Lakes, N.J.)3 seeded at $1 \times 10^4$ into 10 cm culture dishes (Costar, Cambridge, Mass.), and cultured with alpha-Modification of Eagle's Medium (GIBCO/Invitrogen, Carlsbad, Calif.) supplemented with 15% FBS (Equitech-Bio Inc., Kerrville, Tex.), 100 µM L-ascorbic acid 2-phosphate (WAKO, Tokyo, Japan), 2 mM L-glutamine (Biosource/Invitrogen), 100 U/ml penicillin and 100 µg/ml streptomycin at 37° C. in 5% $CO_2$. To assess colony-forming efficiency, day 10 cultures were fixed with 4% formalin, and then stained with 0.1% toluidine blue. Aggregates of ≥50 cells were scored as colonies. The proliferation rate of sub-confluent cultures (first passage) of SCAP was assessed by BrdU incorporation for 6 hours, using BrdU staining Kit (Zymed/Invitrogen). Conditions for the induction of calcium accumulation were as reported previously (18). Calcium accumulation was detected by 2% Alizarin Red S (pH 4.2) staining. The induction of adipogenesis was as previously reported (8). DPSCs and PDLSCs were isolated and cultured as previously described (8, 9). In some experiments, SCAP, DPSCs, and PDLSCs were obtained from the same donor or donors. All primary cells used in this study were at 1-3 passages. For each experiment, same passage of SCAP, DPSCs3 and PDLSCs were used.

Antibodies

Rabbit antibodies included anti-HSP90 (Santa Cruz Biotechnology, Inc., Santa Cruz, Calif.); anti-Cbfal (EMD Biosciences, Inc., San Diego, Calif.); anti-human-specific mitochondria (Chemicon, Temecula, Calif.). Mouse antibodies included antisurvivin (Santa Cruz Biotechnology, Inc.); anti-DSP (LF-21) (Dr. Larry Fisher, NIDCR/NIH); anti-CD 146 and STRO-I (Dr. Stan Gronthos, Institute of Medical and Veterinary Science, Australia). Rabbit and murine isotype-matched negative control antibodies were obtained from Caltag Laboratories (Caltag/Invitrogen). For flow cytometric analysis, R-PE conjugated monoclonal anti-human antibodies include: CD 14, CD18, CD24, CD29, CD34, CD35, CD73, CD90, CD105, CD106, CD146, CD150, CD166 were purchased from Pharmingen/BD Bioscience (San Jose, Calif.) and monoclonal anti-human ALP was from Hybridoma Bank (Iowa University, Iowa).

Transplantation

Approximately $4.0 \times 10^6$ of in vitro expanded SCAP, DPSCs, and PDLSCs were mixed with 40 mg of HA/TCP ceramic particles (Zimmer Inc, Warsaw, Ind.) and then transplanted subcutaneously into the dorsal surface of 10-week-old immunocompromised beige mice (NIH-bg-nu/nu-xid, Harlan Sprague Dawley, Indianapolis, Ind.) as previously described (8, 9, 18, 19). These procedures were performed in accordance with specifications of approved animal protocols (NIDCR #04317 and USC #10874). The transplants were recovered after 8 weeks, fixed with 4% formalin, decalcified with buffered 10% EDTA (pH 8.0), and then embedded in paraffin. Sections were deparaffinized and stained with H&E.

Immunohistochemistry

Deparaffinized sections were immersed in 3% H2O2/methanol for 15 minutes to quench the endogenous peroxidase activity, and incubated with primary antibodies (1:200 to 1:500 dilution). Isotype-matched control antibodies were used under the same conditions for 1 hour. For enzymatic immunohistochemical staining, Zymed SuperPicTure polymer detection kit (Zymed/Invitrogen) was used according to the manufacturer's protocol. Subsequently, sections were counterstained with hematoxylin.

Telomerase Activity

Telomerase activity in SOAP, DPSCs and BMSSCs was detected by using a quantitative telomerase detection kit (Allied Biotech, Inc., Ijamsville, Md.) according to the manufacture's protocol for real time PCR. Briefly, the telomerase in the cell extract from $1 \times 10^5$ cells of SOAP, DPSCs, or BMSSCs added telomeric repeats (TTAGGG) onto the 3' end of the substrate oligonucleotide and iQ SYBR Green Supermix (BioRad Laboratories, Hercules, Calif.), and amplified with an iCycler iQ real-time PCR machine (BioRad Laboratories). The generated PCR products are directly detected by measuring the increase in fluorescence caused by binding of SYBR Green to double-strand DNA and calculated by using an iCycler iQ software (BioRad Laboratories). Some cell extract was heated at 85° C. for 10 minutes and used for negative control. The real-time PCR condition was as follows; telomerase reaction for 20 minutes at 25 C, PCR initial activation step for 3 minutes at 95° C., 3-step cycling; denaturation for 10 seconds at 95° C., annealing for 30 seconds at 60° C., extension for 3 minutes at 72° C., and cycle number 40 cycles.

Population Doubling

SOAP and DPSCs were cultured at low density to form single cell-derived colonies and then were trypsinized and seeded at a density of $0.5 \times 10^4$ cells in 100-mm culture dishes at the first passage. Upon reaching confluency, the cells were trypsinized and seeded at the same cell density. The population doubling was calculated at every passage according to the equation: log2 (the number of harvested cells/the number of seeded cells). The finite population doublings were determined by cumulative addition of total numbers generated from each passage until the cells ceased dividing (20). The criteria for cell senescence are that cells do not divide for a month in culture and that over 60% of the cells are stained positive for beta-galactosidase (18).

Flow Cytometric Analysis

The procedure for flow cytometric analysis was performed as described previously (16). Briefly, cells were trypsinized, and approximately $2 \times 10^5$ cells were pelleted in 5-mL polypropylene tubes (BD Bioscience). They were treated with 5% heat-inactivated FBS, 1% BSA (ICN Biomedicals, Inc., Aurora, Ohio) and 5% normal human serum (Jackson Immuno Research Laboratories, Inc., West Grove, Pa.) in HBSS (GIBCO/Invitrogen) for 30 minutes on ice to block non-specific binding sites. For STRO-I and ALP staining, some of the cells were incubated with 100 [mu]l of STRO-I supernatant (mouse IgM anti-human STRO-I) (16) or mouse IgG1 anti-human bone/liver/kidney ALP (Hybridoma Bank) for 45 minutes on ice. After washing with 5% heat-inactivated FBS in HBSS at 4° C., they were reacted with R-PE conjugated goat F(ab')2 anti-mouse IgM (μ chain specific) (Biosource/Invitrogen) or anti-mouse IgG (H+L) (Southern Biotechnology Associates, Inc., Birmingham, Ala.) for 30 minutes on ice. For CD24 staining, the cells were treated with 1 μg of R-PE conjugated mouse IgG1 antimouse CD24 (BD Bioscience) for 45 minutes on ice. As negative controls, some of the cells were incubated with 1 μg of non-immune mouse IgM (Southern Biotechnology Associates, Inc.) or IgG1 (BD Bioscience). After washing, all of the cells were then sorted on a FACSCalibur flow cytometer (BD Bioscience) by collecting 10,000 events, and analyzed by means of a Cell Quest software (BD Bioscience).

Swine Model

Six inbred male minipigs (4-8 month-old, weighing 20-40 kg) were obtained from the Institute of Animal Science of the Chinese Agriculture University. At this age, minipig incisors are still developing. Minipigs were kept under conventional conditions with free access to water and regularly supply of soft food. This study was reviewed and approved by the Animal Care and Use Committees of Capital University of Medical Sciences and the Institute of Dental and Craniofacial Research. Minipigs were anaesthetized with a combination of ketamine chloride (6 mg/kg) and xylazine (0.6 mg/kg) before the surgery. Minipig SCAP and PDLSCs were isolated and cultured the same as human SCAP and PDLSCs as mentioned above.

Western Blotting

Primary antibodies were used at dilutions ranging from 1:200 to 1:1000. Western blot analyses were carried out as previously reported (18, 21).

Compressive Strength Measurement

Compressive strength was tested by H5KS type force test system with loading of 1 mm/min (Tinius Olsen H5KS testing machine, Tinius Olsen, Ltd., Survey, UK). A newly formed bio-root was harvested six months after transplant, and divided into three pieces. Compressive strength of each piece was measured separately. Compressive strength of natural minipig roots and original HA/TCP carriers were also measured (n=5, each group).

Statistical Analysis

Student t-test was used to analyze the differences between groups. One-way repeated ANOVA followed by Scheffe's comparison was used to compare data from three or more groups. P values less than 0.05 were considered as statistically significant. All statistical data are presented as mean+ SD (n=5).

Example 1

Isolation and Transplantation of SCAP

Figure 1:
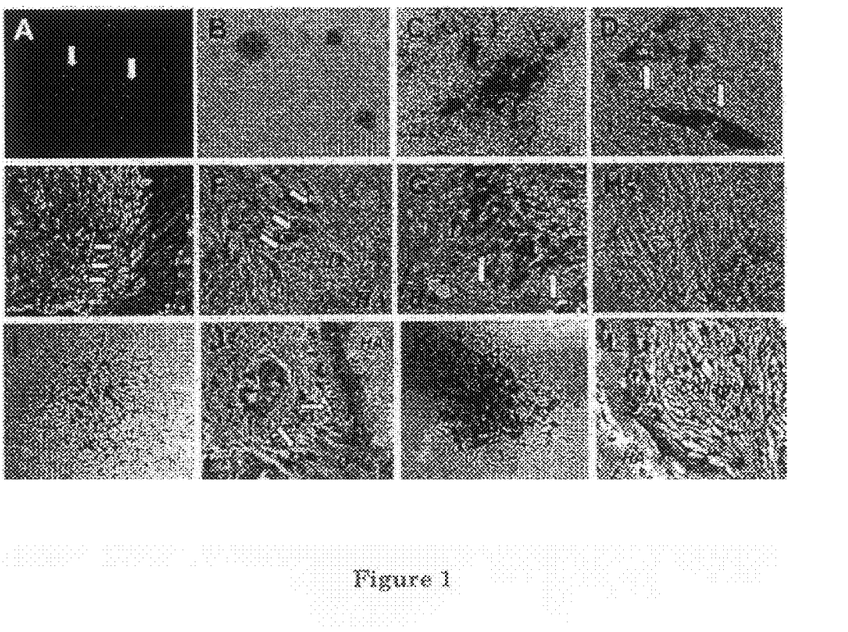

Although the inventors do not wish to be bound to any particular theory of the mechanism by which stem cell progenitors may contribute to root formation, the inventors had found that human root apical papilla tissue on the exterior of the root foramen area demonstrated positive staining for mesenchymal stem cell surface molecule STRO-I (FIG. 1A). The root apical papilla might contain a population of stem/progenitor cells. To identify putative stem cells, single-cell suspensions were generated from human root apical papillae collected from extracted third molars of 18-20 years old adult volunteers; following collagenase/dispase digestion. When cultured at a low cell density, they formed adherent clonogenic cell clusters (CFU-F, colony forming unit, fibroblastic) (FIG. 1B), similar to those observed for various mesenchymal stem cell populations. To investigate the potential of SOAP to undergo odontoblastic/osteoblastic differentiation, multiple colony-derived SOAP at passage two were supplemented with L-ascorbate-2-phosphate, dexamethasone, and inorganic phosphate to induce mineralization in vitro as described previously (8, 9). Small round Alizarin Red-positive nodules formed in the SOAP cultures after four weeks of induction, indicating calcium accumulation in vitro (FIG. 10). Moreover, cultured SOAP were capable of differentiating into other cell types such as adipocytes (FIG. 1D), analogous to DPSCs and bone marrow mesenchymal stem cells (BMMSCs) (8).

To validate the capacity of SOAP to differentiate into functional dentinogenic cells, ex vivo expanded-S CAP were transplanted into immunocompromised mice, with hydroxyapatite/tricalcium phosphate (HA/TCP) as a carrier. A typical dentin structure was regenerated, in which a layer of dentin tissue formed on the surface of the HA/TCP along with connective tissue (FIG. 1E). The newly formed dentin was positive for anti-DSP antibody staining, and dentin-forming cells stained with anti-human-specific mitochondria antibody (FIG. 1F-H), suggesting that the donor derived human SOAP had formed the dentin in vivo. In order to prepare for autologous dental stem cells for functional tooth regeneration in swine, we isolated single colony-derived swine SOAP and PDLSCs and transplanted them into immunocompromised mice to regenerate dentin and cementum, respectively (FIG. 1I-1L), equivalent to that of human SOAP and PDLSCs.

Figure 2:
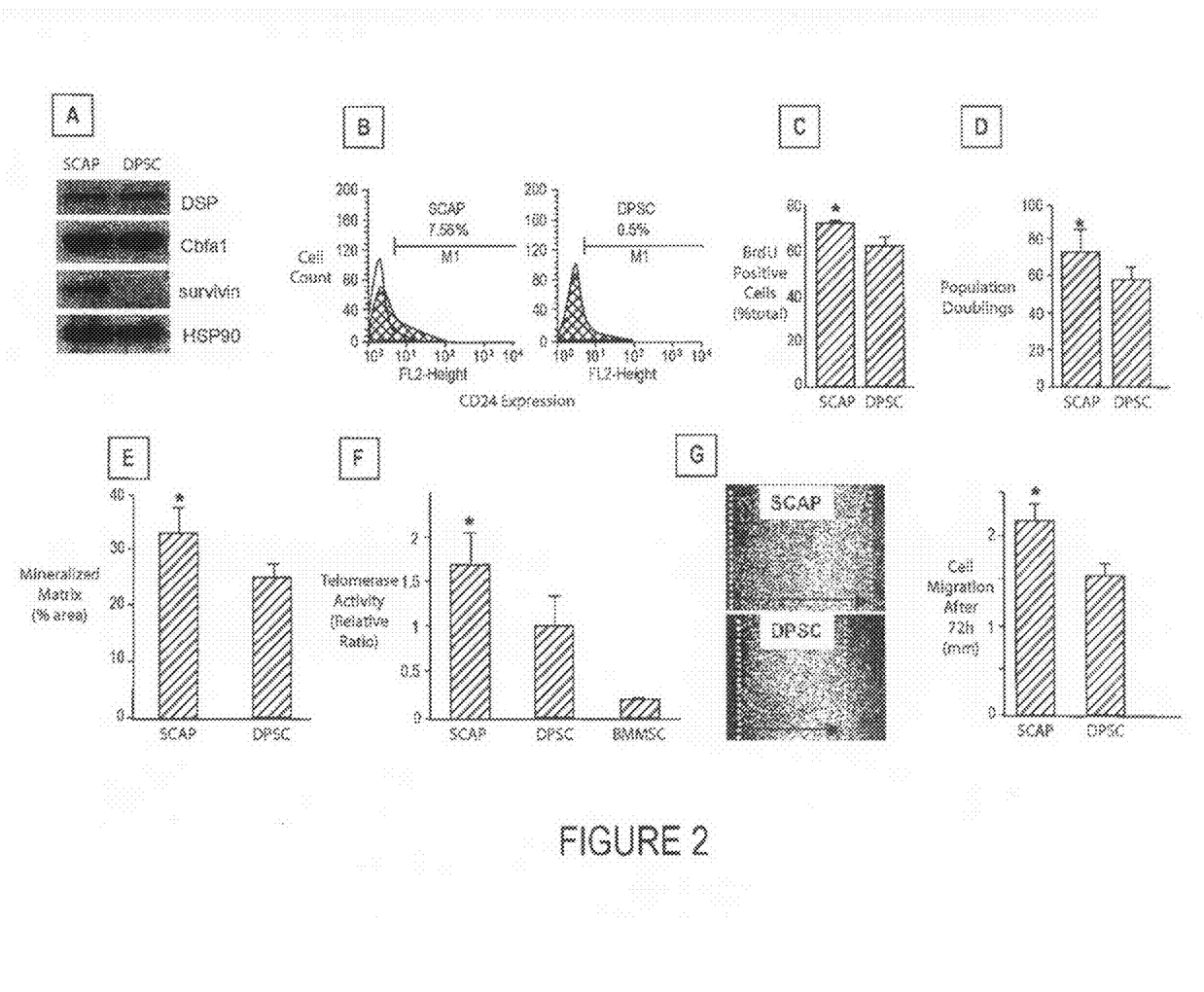
Figure 3:
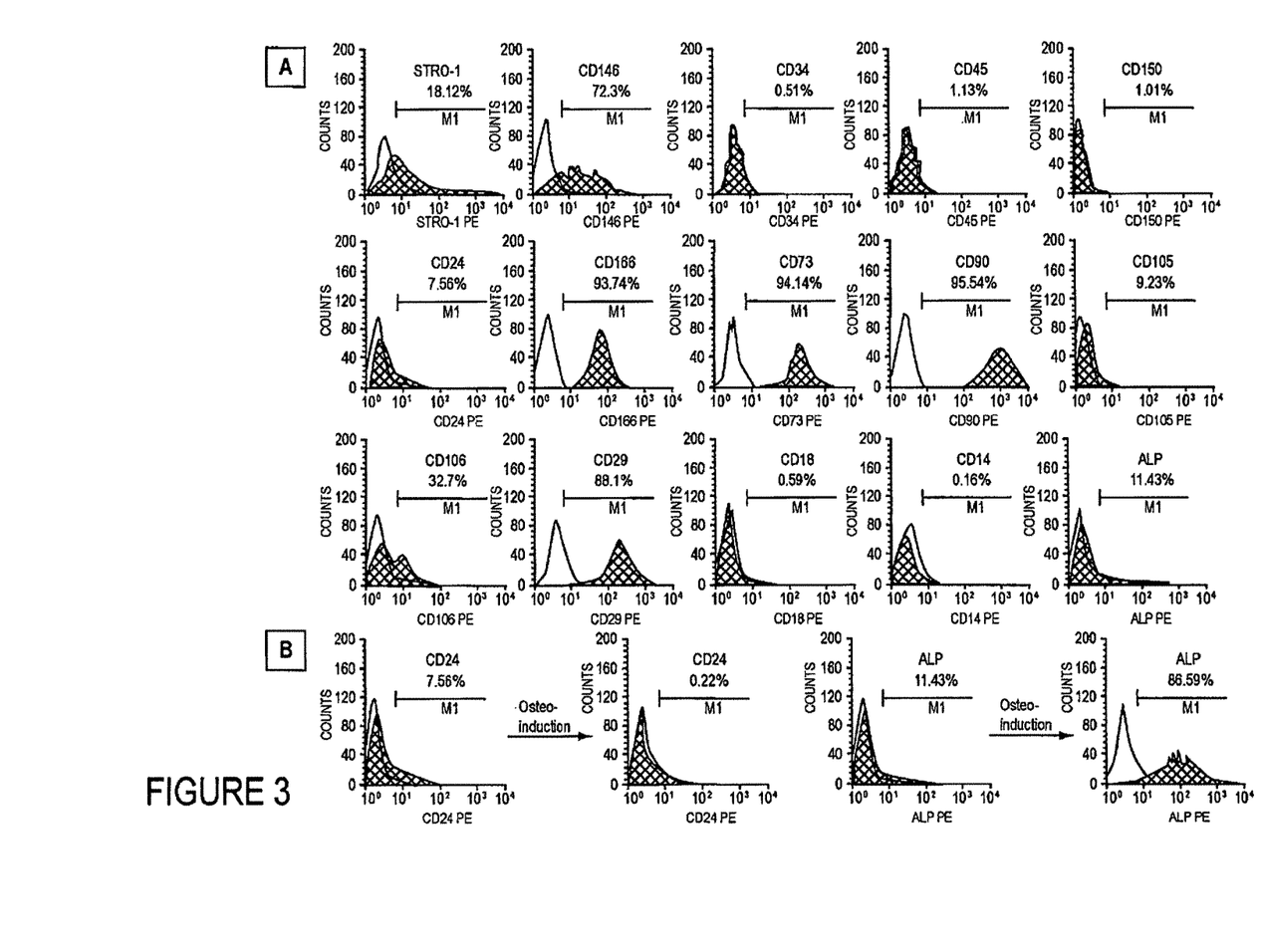

We next addressed whether SOAP and DSPCs were the same or distinct mesenchymal stem cell populations, because both expressed osteo/odontogenic markers and generate mineralized tissue when transplanted into immunocompromised mice. First, we collected SOAP and DPSCs from the same human tooth and grew them under exactly same conditions. According to a cDNA microarray profile comparison (data not shown), there are many genes differentially expressed between these two stem cell populations. Among these genes, we selected survivin as one example, and confirmed its higher expression in SCAP by western blot (FIG. 2A). We also identified that CD 24 as a specific surface marker of SCAP by flow cytometric analysis (FIG. 2B). During odontogenic differentiation in vitro, SOAP lost the expression of CD24 with an up-regulated expression of alkaline phosphatase (ALP) (FIG. 3B). In addition, SOAP showed a significantly higher rate of bromodeoxyuridine (BrdU) uptake (FIG. 2C), and increased number of population doublings (FIG. 2D). The SCAP population also demonstrated an elevated tissue regeneration capacity (FIG. 2E), higher telomerase activity than that of DPSCs from the same tooth (FIG. 2F), and an improved migration capacity in a scratch assay (FIG. 2G), when compared to DPSCs from the same tooth. Collectively, these studies suggested that SOAP are a unique population of postnatal stem cells distinct from DPSC.

Example 2

Surface molecule characterization of SCAP To characterize SCAP by surface molecules, flow cytometric analysis was used to demonstrate that SCAP at passage 1 expressed many surface markers including STRO-1, ALP, CD24, CD29, CD73, CD90, CD105, CD106, CD146, CD166 and ALP but were negative for CD34, CD45, CD18 and CD150 (FIG. 3A). STRO-I and CD146 have been identified as early mesenchymal stem cell markers present on both BMMSCs and DPSCs (8, 16). It was found that CD24 appears to be a specific marker for SCAP, not detectable in other mesenchymal stem cells including DPSCs and BMMSCs (data not shown). In response to osteogenic induction conditions in culture, SCAP begin to down regulate their expression of CD24 while gaining expression of ALP (FIG. 3B).

The experimental evidence suggests that SCAP derived from a developing tissue may represent a population of early progenitors that have advantages for use in tissue regeneration.

Example 3

Functional Tooth Regeneration

Figure 4:
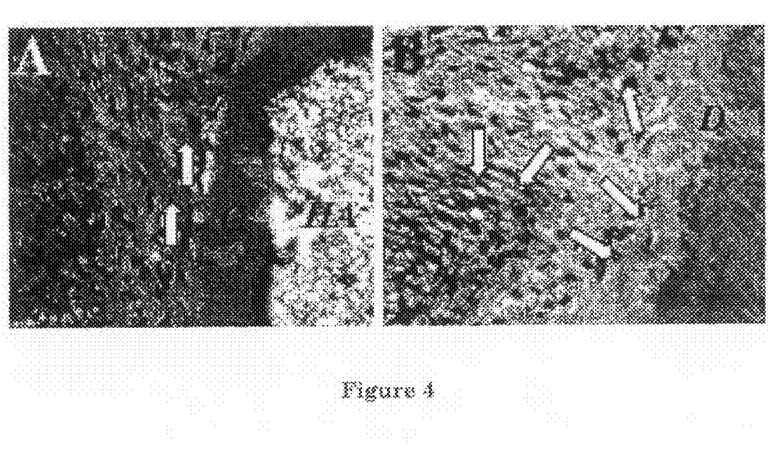
FIG. 4 illustrates the combined human SCAP/PDLSC-mediated tissue regeneration. (A) On the outside of the HA/TCP carrier (HA), PDLSCs can form structures resembling Sharpey's fibers (arrows) connecting with newly formed cementum (C) on the surface of HA/TCP particles (HA). (B) Immunohistochemical staining showed that SCAP/PDLSC-generated tissues were positive for human specific mitochondria antibody staining (arrows).

Identification of SCAP provides an opportunity to pursue root regeneration using this high-quality "young" postnatal stem cell derived from 18-20 years old adult volunteers. To play a functional role in vivo, the root has to connect with the periodontal ligament to ensure correct positional stability and support in situ. Therefore, both human SCAP and PDLSCs were used to generate dentin and PDL on a HA/TCP carrier, in order to mimic a bio-physiological root/periodontal set-up in vivo. Eight weeks after transplantation, the human PDLSCs were able to form cementum on the surface of HA/TCP carrier and Sharpey's fibers, characterized histologically to have collagen fibers anchored into the cementum (FIG. 4 A, B). These data suggested that use of combined mesenchymal stem cell populations provide a basis for root/periodontal tissue regeneration.

Figure 5:
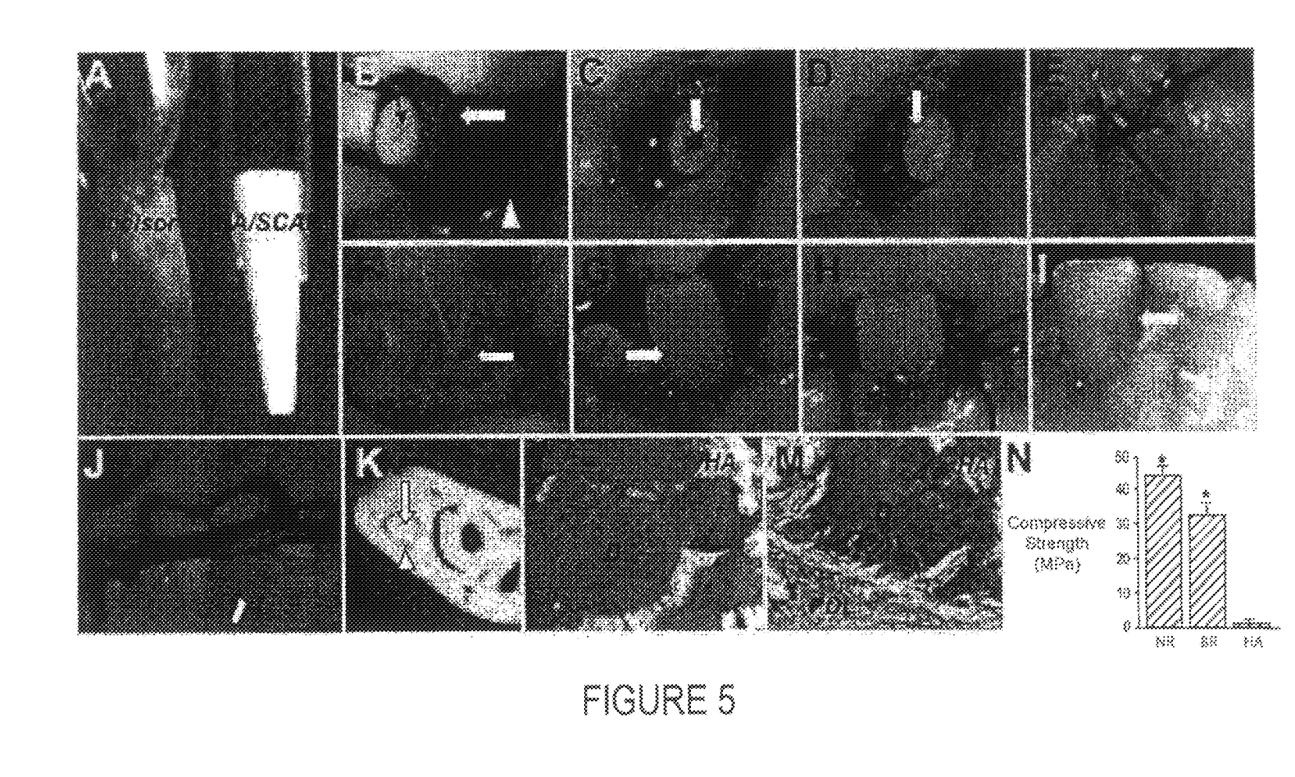

To accomplish functional tooth regeneration, swine was used because of the similarities in swine and human orofacial tissue organization. Swine SCAP were loaded into a root-shaped HA/TCP block that contained an inner post channel space to allow the subsequent installation of a porcelain crown (FIG. 5A). A lower incisor was extracted and the extraction socket was further cleaned with a surgical bur to remove remaining periodontal tissues (FIG. 5A). The HA/TCP block containing SCAP was coated with Gelfoam (Pharmacia Canada Inc., Ontario, Canada) containing PDLSCs and inserted into the socket and sutured for 3 months (FIG. 5B-E). CT examination revealed a HA/SCAP-Gelfoam/PDLSC structure growing inside the socket with mineralized rootlike tissue formation and periodontal ligament space. The surface of the implanted HA/SCAP-Gelfoam/PDLSC structure was surgically re-opened at three months post-implantation; and a pre-fabricated porcelain crown resembling a minipig incisor was inserted and cemented into the pre-formed post channel inside the HA/TCP block (FIG. 5F-H). After suture of the surgical opening, the porcelain crown was retained in situ and subjected to the process of tooth function for four weeks (FIG. 5I, J). CT and histologic analysis confirmed that the root/periodontal structure had regenerated (FIG. 5K-M).

Moreover, newly formed bio-roots demonstrated a significantly improved compressive strength than that of original HA/TCP carriers after six-month implantation (FIG. 5N). These findings suggest the feasibility of using a combination of autologous SCAP/PDLSCs in conjunction with artificial dental crowns for functional tooth regeneration.

Discussion

Through a series of experimentation as described above, the inventors have unexpectedly found that the root apical papilla contained mesenchymal stem cells that have a greater capacity for dentin regeneration than DPSCs. Thus, SCAP represent a novel population of multipotent stem cells as demonstrated by their capacity to develop into odontoblast-like cells and adipocytes in vitro. This cell population was found to express high levels of survivin and telomerase, which are both important molecules in mediating cell proliferation. In addition, CD24, marker for undifferentiated SCAP is found to be downregulated following odontogenic differentiation. These data support the notion that SCAP is a unique type of postnatal stem cells.

Although dental pulp contains DPSCs with dentin/pulp regenerative capacity, developing tissue-derived SCAP showed a superior tissue regeneration potential than that of DPSCs. SCAP collected from just one tooth are capable of providing a large number of stem cells which may be sufficient for human transplantation because they have high proliferative potential as is reflected in high telomerase activity (17). Human SCAP-mediated tissue regeneration may form the basis of cell-based therapy for root regeneration.

Since most human tissue at the developing stage is not clinically available for stem cell isolation, this apical papilla stem cell population, accessible in dental clinical practice, is unusual. SCAP can be isolated from extracted wisdom teeth. Therefore, banking these high quality dental stem cells for future autologous use is also contemplated.

The inventors also contemplate using allogeneic cells as another resource of stem cells for treating those aged individuals who have already had their wisdom teeth extracted, however the immunogenicity of these cells requires further study.

Although newly formed bio-roots show a lower compressive strength than that of natural swine root dentin, they seemed capable of supporting porcelain crown and resulted in normal functions. It may be possible to improve the compressive strength and hardness of the bio-roots by selecting optimal bioengineered materials and by optimizing the implanted stem cell numbers and quality.

Stem cell-mediated root regeneration hybridized with clinical crown technology, as set forth in the present invention, offers a novel approach for functional tooth restoration. It has the advantage of benefiting from the availability of high-quality dental stem cells for autologous transplantation as well as long-term experience with clinical dental implant procedures. In addition, the orofacial region is an open system for directly delivering stem cells for tissue engineering. Furthermore, the minipigs example of the present invention offer an excellent translational model as a research tool for the concept of functional tooth regeneration and the feasibility of using autologous stem cells for transplantation.

REFERENCES

1. Chai Y, Slavkin H C (2003) Prospects for tooth regeneration in the 21st century: a perspective. Microsc Res Tech 60:469-479.
2. Thesleff I (2003) Developmental biology and building a tooth. Quintessence Int 34:613-620.
3. Yen A H, Sharpe PT (2006) Regeneration of teeth using stem cell-based tissue engineering. Expert Opin Biol Ther 6:9-16.
4. Duailibi M T, Duailibi S E, Young C S, Bartlett J D, Vacanti J P, Yelick P C (2004) Bioengineered teeth from cultured rat tooth bud cells. J Dent Res 83:523-528.
5. Ohazama A, Modino S A, Miletich I, Sharpe P T (2004) Stem-cell-based tissue engineering of murine teeth. J Dent Res 83:518-522.
6. Shi S, Bartold P M, Miura M, Seo B M, Robey P G, Gronthos S (2005) The efficacy of mesenchymal stem cells to regenerate and repair dental structures. Orthod Craniofac Res 8:191-199.
7. Young C S, Abukawa H, Asrican R, Ravens M, Troulis M J, Kaban L B, Vacanti J P, Yelick P C (2005) Tissue-engineered hybrid tooth and bone. Tissue Eng 11:1599-1610.
8. Gronthos S, Mankani M, Brahim J, Robey P G, Shi S (2000) Postnatal human dental pulp stem cells (DPSCs) in vitro and in vivo. Proc Natl Acad Sci USA 97:13625-13630.
9. Seo B M, Miura M, Gronthos S, Bartold P M, Batouli S, Brahim J, Young M, Robey P G, Wang C Y, Shi S (2004) Investigation of multipotent postnatal stem cells from human periodontal ligament. Lancet 364:149-155.
10. Tummers M, Thesleff I (2003) Root or crown: a developmental choice orchestrated by the differential regulation of the epithelial stem cell niche in the tooth of two rodent species. Development 130:1049-1057.
11. Eckert S E, Choi Y G, Sanchez AR3 Koka S (2005) Comparison of dental implant systems: quality of clinical evidence and prediction of 5-year survival. Int J Oral Maxillofac Implants 20:406-415.
12. Heitz-Mayfield L J, Lang N P (2004) Antimicrobial treatment of peri-implant diseases. Int J Oral Maxillofac Implants 19 Suppl:128-139.
13. Park S H, Wang H L (2005) Implant reversible complications: classification and treatments. Implant Dent 14:211-220.
14. Larsen M O, Rolin B (2004) Use of the Gottingen minipig as a model of diabetes, with special focus on type 1 diabetes research. liar J 45:303-313.
15. Millikan L E, Boylon J L, Hook R R, Manning P J (1974) Melanoma in Sinclair swine: a new animal model. J Invest Dermatol 62:20-30.
16. Shi S, Gronthos S (2003) Perivascular niche of postnatal mesenchymal stem cells in human bone marrow and dental pulp. J Bone Miner Res 18:696-704,
17. Shi S, Gronthos S, Chen S, Counter C, Robey P G, Wang C-Y (2002) Bone formation by human postnatal bone marrow stromal stem cells is enhanced by telomerase expression. Nat Biotechnol 20:587-591.
18. Miura M, Gronthos S, Zhao M, Lu B, Fisher L W, Robey P G, Shi S (2003) SHED: stem cells from human exfoliated deciduous teeth. Proc Natl Acad Sci USA 100:5807-5812.
19. Krebsbach P H, Kuznetsov S A, Satomura K5 Emmons RV3 Rowe D W, Robey P G (1997) Bone formation in vivo: comparison of osteogenesis by transplanted mouse and human marrow stromal fibroblasts. Transplantation 63:1059-1069.
20. Blazer S, Khankin E5 Segev Y, Ofir R, Yalon-Hacohen M, Kra-Oz Z5 Gottfried Y5 Larisch S, Skorecki K L (2002) High glucose-induced replicative senescence: point of no return and effect of telomerase. Biochem Biophys Res Commun 296:93-101.
21. Shi S, Robey P G, Gronthos S (2001) Comparison of human dental pulp and bone marrow stromal stem cells by cDNA microarray analysis. Bone 29:532-539.

What is claimed is:

1. A method for repairing a damaged tooth in a human subject, comprising:
   (i) obtaining root apical papilla from a tooth extracted from an adult human;
   (ii) generating a single cell suspension from the root apical papilla;
   (iii) culturing the single cell suspension to form adherent clonogenic cell clusters of human stem cells from apical papilla (SCAP), wherein the SCAP comprise cells that express STRO-1, CD146, CD166 and about 7.5% CD24+ cells;
   (iv) expanding SCAP ex vivo;
   (v) providing a biocompatible carrier;
   (vi) loading the biocompatible carrier with the expanded SCAP;
   (vii) coating said SCAP loaded biocompatible carrier with human periodontal ligament stem cells (PDLSC) embedded in a gelatin solution, wherein the gelatin solution adheres to the surface of the SCAP loaded biocompatible carrier;
   (viii) extracting the damaged tooth from the human subject's oral cavity, wherein upon extraction of the damaged tooth, an extraction socket is formed in its place;
   (ix) cleaning the extracted socket and implanting the biocompatible carrier that is loaded with SCAP and coated with PDLSC into the socket; allowing sufficient time for the SCAP and PDLSC to form a bio-root incorporating the biocompatible carrier; and
   (x) surgically exposing the bio-root and affixing a prefabricated crown resembling the damaged tooth onto the bio-root.

2. The method of claim 1, wherein the biocompatible carrier is hydroxyapatite tricalcium (HA).

3. The method of claim 1, wherein the crown is a ceramic crown.

4. The method of claim 3, wherein said ceramic is porcelain.

5. The method of claim 1, wherein said SCAP are isolated from an extracted human wisdom tooth.

6. The method of claim 1, wherein the biocompatible carrier is a biocompatible carrier formed in a shape resembling a root of the damaged tooth.

7. The method of claim 1, wherein the biocompatible carrier has an inner post channel space.

8. The method of claim 1, wherein the human SCAP are autologous human SCAP.

* * * * *